United States Patent [19]
Pryor et al.

[11] Patent Number: 5,890,687
[45] Date of Patent: Apr. 6, 1999

[54] FOLDABLE WHEELED STAND

[75] Inventors: Paul E. Pryor, Oceanside; Jeffery W. Pryor, Vista; Jack Ratcliff, Carlsbad, all of Calif.

[73] Assignee: Pryor Products, Oceanside, Calif.

[21] Appl. No.: 684,632

[22] Filed: Jul. 22, 1996

[51] Int. Cl.$^6$ .................................................. F16M 13/00
[52] U.S. Cl. ...................... 248/158; 280/42; 248/125.8; 248/166; 248/167
[58] Field of Search ................. 280/42, 646, 47.35, 280/79.5, 79.2; 248/158, 166, 167, 434, 435, 439, 168, 170, 176.1, 125.8, 129, 292.12

[56] References Cited

U.S. PATENT DOCUMENTS

| | | | |
|---|---|---|---|
| 354,350 | 1/1886 | Pryor et al. | D24/128 |
| 2,629,607 | 2/1953 | Roubeck | 280/42 |
| 2,639,162 | 5/1953 | Schon | 280/42 |
| 2,677,518 | 5/1954 | Happy et al. | 248/125.7 |
| 2,921,763 | 1/1960 | Miller et al. | 248/167 |
| 2,990,764 | 7/1961 | Wilder | 248/129 |
| 3,173,642 | 3/1965 | Greenspan | 248/170 |
| 3,847,335 | 11/1974 | Ross | 248/166 |
| 3,970,344 | 7/1976 | Baumann | 297/189 |
| 4,086,932 | 5/1978 | Richardson | 135/67 |
| 4,332,378 | 6/1982 | Pryor | 272/70.3 |
| 4,561,414 | 12/1985 | Nozato | 124/78 |
| 4,744,536 | 5/1988 | Bancalari | 248/125.8 |
| 4,892,279 | 1/1990 | Lafferty et al. | 248/125.8 |
| 5,000,407 | 3/1991 | Juji et al. | 248/125.8 |
| 5,174,533 | 12/1992 | Pryor et al. | 248/288.5 |

*Primary Examiner*—Leslie A. Braun
*Assistant Examiner*—Kimberly T. Wood
*Attorney, Agent, or Firm*—Brown, Martin, Haller & McClain

[57] ABSTRACT

The stand incorporates two pairs of wheels and a support pole carried from a central pivot member. The stand is collapsible from an upright orientation in which all wheels are floor-engaging to a folded orientation in which the wheels lie closely alongside the support pole. The wheels are carried on wheel support elements which in turn are connected to a central pivot member. Folding and collapsing actions are synchronized by control arms that extend between the support pole and wheel support elements.

16 Claims, 3 Drawing Sheets

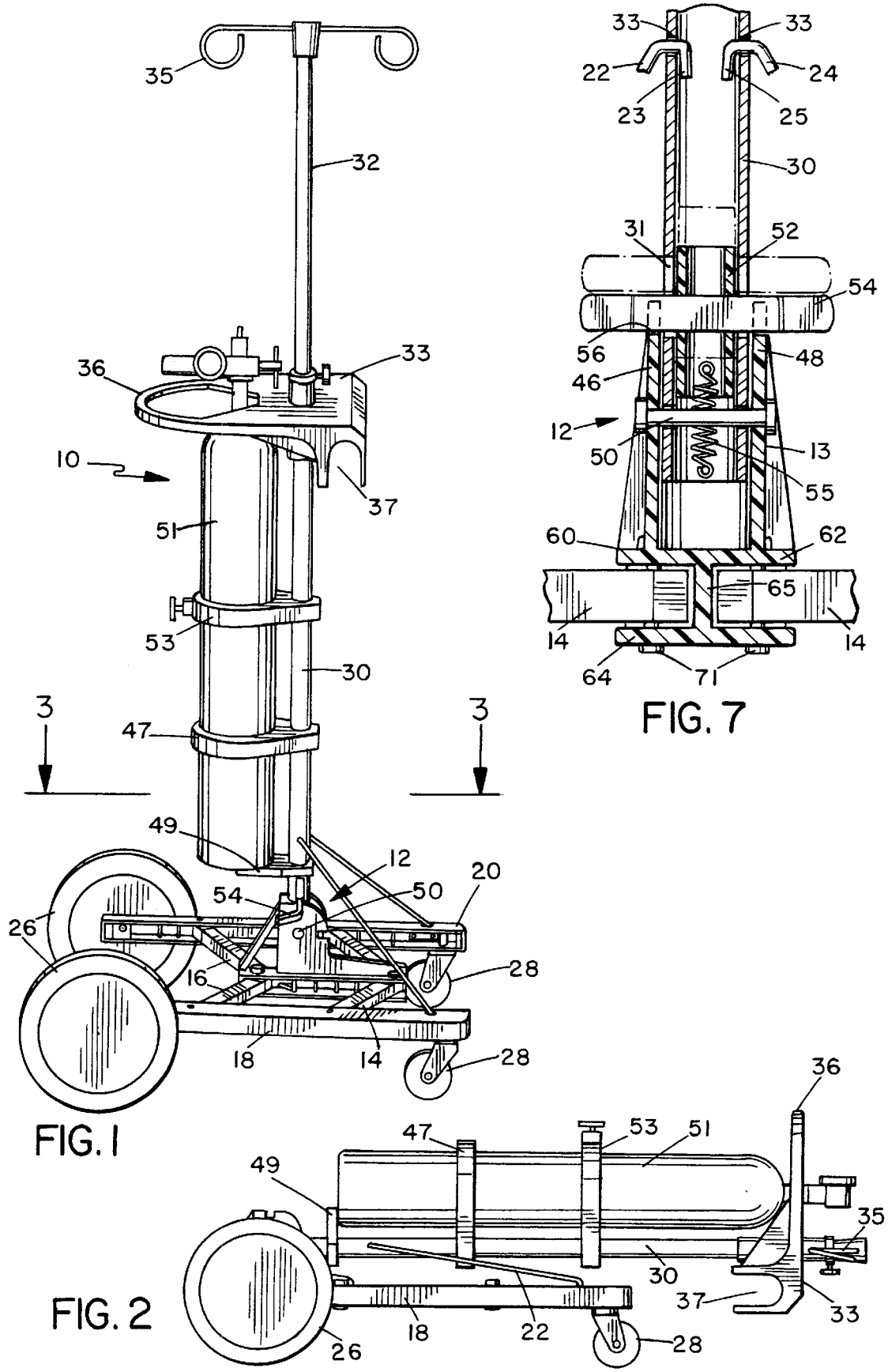

FOLDABLE WHEELED STAND

BACKGROUND OF THE INVENTION

Wheeled IV stands are in use in hundreds of hospitals nationwide. These stands allow IV bags and bottles to be safely supported at a level that will create gravity flow to the patient or to intermediate devices such as IV pumps. There has been a recognition for many years that it is important, to the health of the patient, and to the cost of the delivery of medical services, to provide aids to make it possible for patients to become ambulatory, and self-sufficient, as quickly as possible. As IV stands have evolved, auxiliary functions have been added to accommodate additional functionality such as provisions for ambulatory patient support, and for mounting additional equipment and supplies such as oxygen bottles.

U.S. Pat. No. 4,332,378, which is co-owned with the present invention, is an example of an advance in IV stands that has added additional functionality by providing patient support in the form of a support wheel that allows the patient to use the stand in the manner of a walker while the patient remains connected to IV support.

U.S. Pat. No. 5,337,992, which is also co-owned with the present invention, is a device that allows an IV stand to be supported on a wheeled bed so that the necessary IV support can be conveniently and safely moved with the patient.

While the above features add functionality to IV stands, they nevertheless increase their size and bulk, which creates storage constraints when the stands are not in use, and makes it difficult to transport the stands.

Folding stands, such as that illustrated in U.S. Pat. No. 4,744,536 have been devised which reduce the storage volume of the stand when it is being shipped or stored, but such designs must be carried when collapsed, which requires that ambulatory patients have assistance in navigating stairs and the like. Folding stands, according to prior designs, have also had to compromise strength to achieve folding.

The deficiencies of prior stands are particularly apparent when the stands are used outside of the hospital environment. These deficiencies include the inability of present stands to facilitate the traverse of stairs and other obstacles, and the inability of stands to collapse or collapse sufficiently to allow the stands to be easily transported in vehicles.

Therefore, it is desirable to have a wheeled IV stand that can accommodate a high degree of accessory functionality, and at the same time allow the patient to easily transit stairs and other obstacles, and which can be configured to occupy a small volume when being stored or transported.

SUMMARY OF THE INVENTION

In an exemplary embodiment of the invention, the deficiencies of prior art devices are overcome in a device that utilizes a unique folding action to collapse the stand into a transportable configuration and where the principal functions of the stand can be used during transit. Unlike prior folding stands, the folding action in the present invention reduces both the width and height of the stand. The functionality of the stand is preserved by converting the stand from an upright, self-supporting configuration, to a two-wheeled trailering configuration. Main wheels, used during trailering, are of a sufficiently large diameter so that steps can be traversed. For example, to climb steps, the folded stand is grasped by the patient support handle and the stand pulled upwardly at an angle so that the wheels contact the vertical riser between the stair treads, such that the stand moves alternately vertically and horizontally, one tread at a time. In the upright orientation, the main wheels and secondary wheels are supported in a wide stable stance.

The stand desirably has provision for a completely collapsed configuration that retracts the secondary wheels out of interference with the support handle, so that the stand may be received over the footboard of a bed for transport of the bed, patient and required equipment, together. This configuration and mounting is also useful to reduce the floor space occupied by medical equipment in a patient room.

A central pivot member mounts pivot pins for the IV pole and for folding arms that extend to provide a wide stance for self-standing use, and retract to minimize space for trailering and for storage or transport use. The IV pole pivots between locked positions where the pole is upright for self-standing use or folded for trailering use.

The folding action is synchronized by control arms so that user action to accomplish folding is minimized. The control arms extend from the IV pole to wheel mount elements which are in turn attached to folding arms. When the pole is folded the control arms drive the wheel mount elements longitudinally (horizontally when the wheels are supported on the floor) so that when folding is complete, the wheel mount elements lie parallel to and directly alongside of the support pole. When folded, the stand and attached accessories (such as oxygen bottles) is sufficiently compact to fit in the trunk of most automobiles. This allows compliance with regulations that require separate stowage of oxygen bottles and intravenous dispensing apparatus.

To facilitate shipping, a combined shipping and accessory transport container is provided. In the exemplary embodiment, the container is a rigid box that has openings for the main wheels. During shipping, these openings are blocked. Upon arrival at a destination, the openings are unblocked and the stand shifted in the box so that the wheels protrude through the openings. This allows the stand to be operated in the trailering mode while still in the shipping container. In this manner, the accessories and supplies, such as IV bags and pumps, may be stored in the box when the stand is wheeled, for example, to and from a vehicle. As an alternative to a rigid box, a folding bag with the necessary wheel openings may be utilized.

It is therefore advantageous to have a wheeled stand that collapses without, at the same time, becoming non-functional. Another advantage of the invention is to have a wheeled stand that may be operated in either an upright, self-supporting or a trailering mode. It is another advantage to provide further collapsing of the stand such that the wheels are retracted out of interference with bed mount devices carried on the stand. Other advantages include a design that is high in strength but may be made out of low cost materials by high production rate machinery. Still another advantage is the ease of operation of the device between folded and fully erect, self-standing positions. A further advantage is the provision for high durability in the moving parts of the stand, including the pivots and latches utilized with the invention.

BRIEF DESCRIPTION OF THE DRAWINGS

FIG. 1 is a perspective view of the wheeled stand in fully erect position;

FIG. 2 is a side elevation view of the stand in collapsed position;

FIG. 7 is a sectional view taken on line 7—7 of FIG. 6.

DETAILED DESCRIPTION OF THE DRAWINGS

Figure 3:
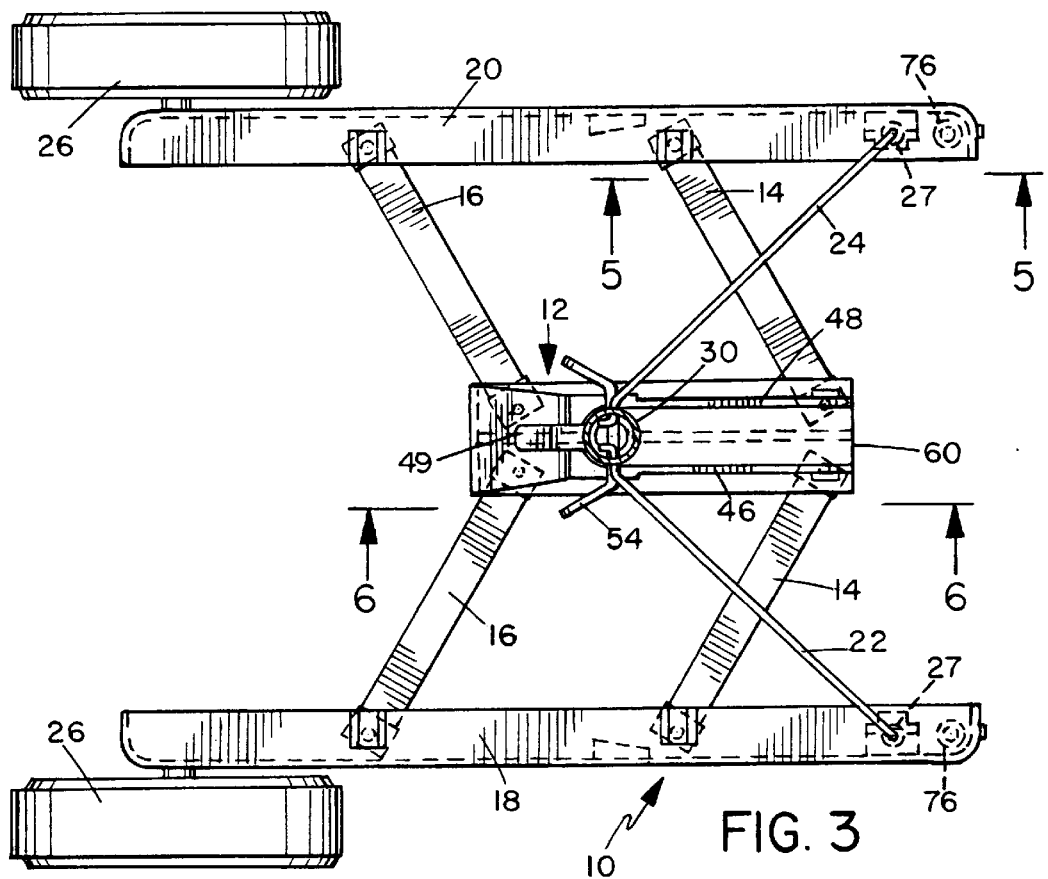
FIG. 3 is an enlarged sectional view taken on line 3—3 of FIG. 1.

Referring now to the drawings, and particularly FIG. 1, there is illustrated a foldable stand 10 which is in the upright or self-supporting configuration. In this configuration, the stand is intended to operate in a manner comparable to conventional wheeled stands. Main wheels 26 and secondary wheels 28 are carried on wheel mount elements 18 and 20 to provide a wide, stable platform. A support pole 30 with a telescoping IV pole extension 32, supports, IV bags or bottles carried on the hanger 35. A patient support handle 36, on support device 33, allows ambulatory patients to use the stand both for transport of the necessary medical equipment and for ambulatory support. When used for ambulatory support, the patient grasps the handle 36 and walks with their feet between the wheels 26. Opposite the handle 36 is a downwardly opening channel 37 which may be received over a horizontal support such as the footboard of a patient bed. In addition to intravenous fluid containers, other equipment, such as IV pumps and the like, may be carried on the stand. It is specifically contemplated that an oxygen bottle 51 may be retained and positioned on the stand. For supporting oxygen bottles, a bracket 49 is attached to pole 30. Positioning ring 47 and locking ring 53 are spaced from the bracket 49. The bracket and rings may be removed when not in use. Although the use of large main wheels 26 and smaller secondary castering wheels 28 have special advantages when utilized during patient-assisted transit and in the transportation of the device, it is also possible to utilize the stand with four or more castering wheels, as is more conventional in the hospital-only environment.

Figure 6:
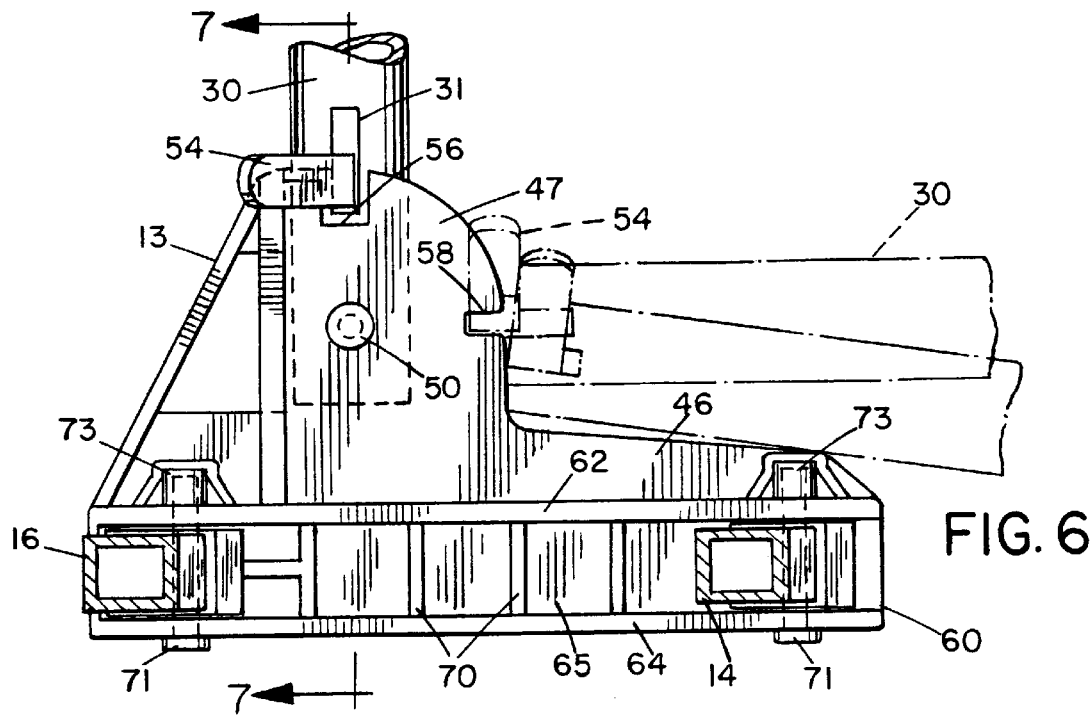
FIG. 6 is an enlarged view taken on line 6—6 of FIG. 3.

A principal feature of the invention is the ability to fold and collapse from the wide stance and upright configuration in FIG. 1 to the folded and collapsed configuration in FIG. 2. The pivot member 12 illustrated in FIG. 1 and more particularly in FIGS. 6 and 7 has structural features that make it possible to accomplish many of the folding and collapsing operations and to do so in a manner that makes it possible for the stand to be operated easily by service providers or patients. The pivot member 12 is designed so that it can be molded out of high-strength materials in a single molding operation. The pivot member is generally comprised of an upper pivot mount 13 and a base 60. The IV pole 30 is received on the pivot mount 13 through a pole pivot pin 50. The pole is constrained between the pivot mount flanges, of which flange 46 is visible in FIG. 6. In the upright position, a latch operator 54 is received in a latching detent 56. The first step in folding and collapsing the stand is to raise the latch operator 54 free of the detent 56, and then to rotate the pole in a clockwise direction as illustrated in FIG. 6. During the clockwise rotation, the latch operator rides on the smooth arcuate surface 47 of the flanges 46 and 48 until a second detent 58 is engaged. Detent 58 holds the pole in an orientation with the pole parallel to the wheel mount elements 18 and 20 so that the folded configuration corresponds to that in FIG. 2. This configuration is ideal for trailering use of the stand. Withdrawing the latch operator from detent 58 permits continuing rotation to the fully collapsed dotted line configuration illustrated. The fully collapsed configuration folds the supplemental wheels 28 out of interference with the channel 37 so that the entire stand can be supported from the footboard of a bed. This orientation is also ideal for transport in a container. The base 60 extends on both sides of the axis of the pivot pin in a direction transverse to the axis. Folding arms 14 and 16 are mounted near opposite ends of the base 60. The folding arms are pivotally connected to the wheel mount elements 18 and 20.

Control arms 22 and 24 extend from the pole 30 to the wheel mount elements, collapsing the stand during the folding operation. As the pole is rotated for collapsing the stand, the control arms 22 and 24 cause the wheel mount elements 18 and 20 of the base 11 to rotate about their pivot pins in the arms 14 and 16. The arms 14 and 16 rotate about their pivot mounting on the base 60 to assume the collapsed configuration in FIG. 4.

Figure 4:
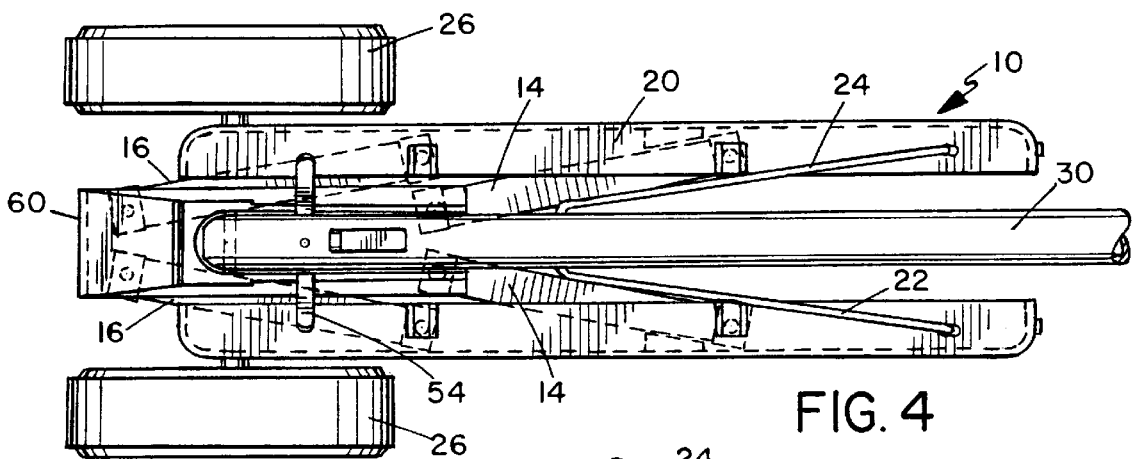
FIG. 4 is a view similar to FIG. 3 but with the stand collapsed.

Referring now more particularly to FIGS. 3 and 4, the geometry which permits coordinated collapsing action to take place simultaneously with the folding of the IV pole will become more apparent. The pivot member 12 mounts folding arms 14 and 16. In the exemplary embodiment, four folding arms are illustrated. The two folding arms 14 are spaced longitudinally from the second pair of folding arms 16. Both sets of arms are attached through pivot pins to the central pivot member 12, as will appear in greater detail from subsequent discussion of FIGS. 6 and 7. The arms 14 and 16 carry, at their outer ends, wheel mount elements 18 and 20. Wheel mount elements 18 and 20 are illustrated to comprise generally straight, elongated channels which extend all the way from the portion mounting the main wheel 20 to the portion mounting the castering wheels 28. However, it will be appreciated that curved or other configurations are possible as long as the arms 14 and 16 are structurally interconnected with the wheels through the wheel mount elements or other structural interconnection for coordinated movement.

Figure 5:
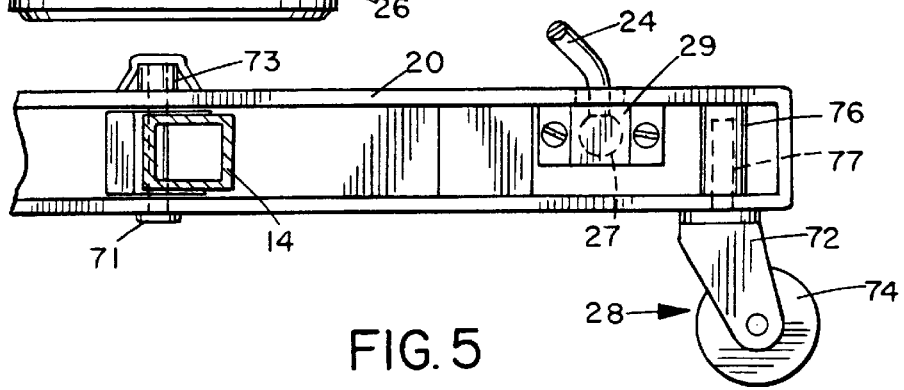
FIG. 5 is an enlarged view taken on line 5—5 of FIG. 3.

As will appear in FIG. 3, it is advantageous to mount the wheel mount elements and control arms such that, in the erect configuration, the central pivot member is displaced (to the right in FIG. 3) as far as possible to provide maximum clearance for use of the stand as a walker. This is accomplished by mounting the pivot member such that the arms 14 and 16 rotate past the perpendicular to the point that the central pivot member 12 is offset from the medial center of the structure. When the collapsing action takes place, as illustrated in FIG. 4, the pivot mount is driven by the control arms 22 and 24 all the way from its rightward overcenter position illustrated in FIG. 3 to a position where the bulk of the pivot member is directly between the main wheels. This lowers the center of gravity in the folding orientation and allows the device to be utilized in a trailering mode without interference between the central pivot member and the main wheels which are used in the trailering operation. The control arms 22 and 24 facilitate this collapsing aspect of the invention by forcing the wheel mount elements in a rightward direction in FIG. 3 during pivoting folding of the IV pole which causes the arms 14 and 16 to rotate through more than 90° until they are fully collapsed and partially received within the channel structure of the wheel mount elements 1 8 and 20 as shown in FIG. 4. The necessary rotation of the control arms 22 and 24 during the collapsing operation is accommodated by registering arcuate terminuses 23 and 25 (see FIG. 7) in holes 33 through the IV pole. It has been found by utilizing stainless control arms and a stainless steel central pole that the relative movement between like, high-strength materials results in a long service life with little wear. The opposed ends of the control arms are received in the molded wheel support elements. Therefore, a bearing structure is provided. Accordingly, the lower terminus of the control arms 22 and 24 mounts a bearing ball (see bearing ball 27 in FIG. 5). The bearing ball is retained for movement on the wheel support elements by a ball retention plates. (See plate 29). In FIG. 5, the manner in which the secondary or castering wheels 28 are mounted is illustrated. A castering pivot boss 76 is molded into the wheel support elements 18 and 20 (element 20 visible in FIG. 5). This pivot boss 76 receives the pivot pin 77 of a caster mount 72. The caster mount positions the castering wheel 74 offcenter from the pivot pins 77 to provide the well-known castering operation.

Referring to FIGS. 6 and 7, the details of the pivot latch operation are illustrated. The latch operator 54 is received through the slot 31 which permits reciprocating action of the operator within the IV pole 30. An internal bushing 52 maintains the alignment of the latch operator as it reciprocates between latched (full line in FIG. 7) and unlatched (dotted line in FIG. 7) positions. A tension spring 55 is secured between the bottom of the bushing 52 and the bottom of pole 30.

In FIG. 7, there is illustrated the manner in which the upright flanges 46 and 48 of the pivot mount 13 restrain the pole 30 so that it is securely and stabley held in either latched position. The base 60 is shown to comprise an upper horizontal flange 62, central upright flange 65 and lower horizontal flange 64. The manner in which the base member cradles and supports the arm 14 (illustrated) and 16 (not visible in this view) will be apparent from FIG. 7. The pivoting of the arms 14 and 16 is made possible by pivot pins 71 which penetrate the upper and lower flanges 62 and 64 and are held in place by retention nuts 73.

Figure 8:
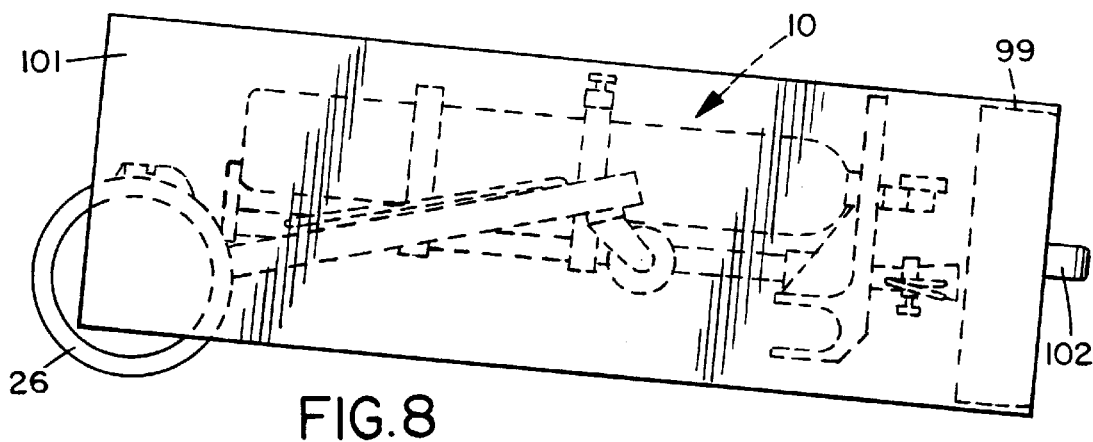
FIG. 8 is a side elevation view showing the stand in a transport and storage box.
Figure 9:
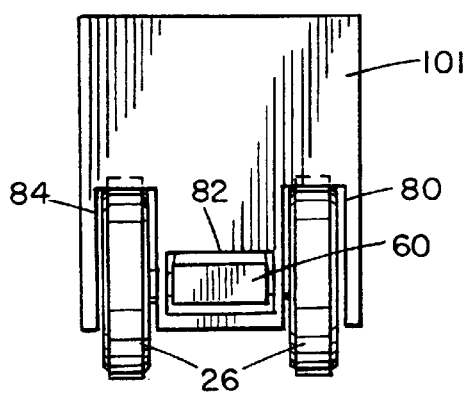
FIG. 9 is a rear view of the box.

Referring again to FIG. 6, the base is shown to be reinforced by a plurality of vertical ribs 70. These ribs are relieved as necessary to allow the folding arms 14 and 1 6 to be cradled between the upper (62) and lower (64) flanges of the base in the fully folded position. The configuration of the fully collapsed stand 12 is illustrated in FIG. 8. So collapsed, the stand fits within a generally cubicle shipping container 101 of minimum profile. Normally blocked openings in 80, 82 and 84 may be unblocked upon arrival at a destination so that the main wheels 26 of the stand protrude from the shipping container. In this way, the shipping container 101 may be utilized to move the stand, accessory equipment and supplies without unpacking. The entire assembly may be moved on the stand's main wheels 26 directly from a vehicle and into a residence, for example. The stand may be held in position with the main wheels protruding from the box by a foam pad 99 which fits within the shipping container 101. Trailering of the stand in the container 101 is facilitated by the inclusion of handle 102.

In use, the stand is operated on flat surfaces in the configuration shown in FIG. 1. For use in the trailering mode, a patient, after collapsing the stand to the FIG. 2 configuration, grasps the patient support handle and rotates the stand past the upright position so that the stand follows the patient and is supported from the main wheels 26 only. Because of the size of the main wheels (at least five inches in diameter) and the clearance they provide over obstacles, it is possible to maneuver the stand over rough surfaces. During these operations, the patient can still be provided with supplemental oxygen and may be on IV support. The large wheels make is possible to negotiate stairs. Typically, stairs are negotiated with the stand preceding the patient going downstairs, and trailering as the patient proceeds upstairs. In each mode, the main wheels alternately contact the tread and riser of the stair so as to move upward in a series of vertical and horizontal increments. If the stand is to be transported, such as in the trunk of a vehicle when being delivered to a patient in home care environment, the stand may be received in an integrated shipping container 101. With the openings 80, 82 and 84 fully blocked, the stand is fully enclosed in the container 101 and protected from damage in transit. The extra space surrounding the stand may be filled with supplies, medical accessories and other materials. Upon arrival at the destination, removal of flat cardboard, or other material blocking the openings allows the stand to be moved within the container so that the main wheels protrude from the openings 80 and 84. The opening 82 is provided for the end of the pivot mount to protrude so as to not interfere with the full extension of the main wheels from the shipping container. Thus, the stand can be wheeled through an airport lobby or from a vehicle to a residence without removing it from the shipping container or unpacking the contents.

Having described our invention, we claim:

1. A foldable wheeled stand comprising:

a central pivot member;

a support pole pivotally received on said pivot member for rotation about a pivot axis between upright and folded positions;

a pivot lock member for selectively engaging said central pivot member when said support pole is pivoted to said upright position;

at least two folding arms mounted on a vertical axis on said central pivot member;

at least two main wheels connected to said folding arms for being positioned in a first erect orientation and in a second folded orientation.

2. The foldable wheeled stand of claim 1, further including:

said pivot member extending longitudinally on both sides of said pivot axis in a direction transverse to said pivot axis.

3. The foldable wheeled stand of claim 2, further including:

a pair of wheel mount elements;

at least four folding arms;

at least two of said folding arms being mounted on longitudinally spaced points on said central pivot member;

said folding arms being pivotally mounted at spaced points on said wheel mount elements;

at least two wheels mounted on each wheel mount element.

4. The foldable wheeled stand of claim 2, wherein:

said wheels extending longitudinally of said central pivot member in said second folded orientation.

5. The foldable wheeled stand of claim 4, wherein:

said main wheels have a diameter of at least five inches.

6. The foldable wheeled stand of claim 2, including:

a support handle attached to and extending longitudinally from said support pole near the upper end of said support pole.

7. The foldable wheeled stand of claim 6, wherein:

said support handle includes a downwardly opening channel spaced from said support pole and having an axis that is parallel to said pivot axis.

8. The foldable wheeled stand of claim 2, wherein:

said pivot lock member selectively engages said central pivot member when said support pole is pivoted to said folded position.

9. The foldable wheeled stand of claim 8, wherein:

said pivot lock member comprises a lock operator that selectively engages an erect locking detent and a folded locking detent in said central pivot member.

10. The foldable wheeled stand of claim 9, wherein:

said pivot member has an arcuate surface which slidably engages said latch operator for movement between said upright and said folded positions.

11. The foldable wheeled stand of claim 10, wherein:

a surface extending beyond said folded locking detent for fully collapsing said pole.

12. The foldable wheeled stand of claim 3, wherein:

said support pole being rotatable beyond said second folded orientation to a fully collapsed orientation.

13. The foldable wheeled stand of claim 12, including:

a support handle attached to and extending longitudinally from said support pole near the upper end of said support pole;

said support handle includes a downwardly opening channel spaced from said support pole and having an axis that is parallel to said pivot axis;

said wheels on said wheel mount elements that are closest to said support handle in said folded orientation are retracted out of interference with said downwardly opening channel in said fully collapsed orientation.

14. The foldable wheeled stand of claim 3, wherein:

a pair of control arms pivotally attached at first ends to said support pole above said pivot member and pivotally attached at second ends to said wheel mount elements at points spaced longitudinally from said pivot axis in said upright orientation.

15. A foldable wheeled stand and container therefore comprising:

a central pivot member on said stand;

a support pole pivotally received on said pivot member for rotation to a folded orientation;

at least two wheels mounted on said central pivot member and being spaced and having their axes aligned when said pole is in said folded orientation;

the container substantially completely enclosing said stand and having at least two openings adjacent an end thereof;

said wheels at least partially protruding through said openings whereby said stand may be supported on said wheels when the opposite end of said container is raised.

16. The foldable wheeled stand of claim 1 wherein:

said pole mounts a plurality of oxygen bottle retention means for supporting and positioning at least one oxygen bottle.

* * * * *